(12) United States Patent (10) Patent No.: US 9,192,483 B1
Radcliffe et al. (45) Date of Patent: Nov. 24, 2015

(54) SPINAL FUSION SYSTEM

(71) Applicant: Amendia, Inc., Marietta, GA (US)

(72) Inventors: Jeffrey Scott Radcliffe, Marietta, GA (US); Michael Glatzer, Alpharetta, GA (US); Mark Wilson Jacob, Acworth, GA (US); Reginald Antonio Terrell, Marietta, GA (US); William Carlton Tally, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 0 days.

(21) Appl. No.: 14/753,284

(22) Filed: Jun. 29, 2015

Related U.S. Application Data

(60) Provisional application No. 62/018,460, filed on Jun. 27, 2014.

(51) Int. Cl.
*A61F 2/44* (2006.01)
*A61B 17/80* (2006.01)

(52) U.S. Cl.
CPC ............... *A61F 2/4455* (2013.01); *A61F 2/442* (2013.01); *A61B 17/8042* (2013.01); *A61F 2220/0016* (2013.01)

(58) Field of Classification Search
CPC .......................... A61F 2/4455; A61B 17/8042
See application file for complete search history.

(56) References Cited

U.S. PATENT DOCUMENTS

| | | | |
|---|---|---|---|
| 4,017,946 A | 4/1977 | Soja | |
| 5,607,426 A | 3/1997 | Ralph et al. | |
| 5,904,683 A | 5/1999 | Pohndorf et al. | |
| 6,258,089 B1 | 7/2001 | Campbell et al. | |
| 6,984,234 B2 | 1/2006 | Bray | |
| 7,955,362 B2 | 6/2011 | Erickson et al. | |
| 8,287,575 B2 | 10/2012 | Muerner et al. | |
| 8,328,872 B2 | 12/2012 | Duffield et al. | |
| 8,425,607 B2 | 4/2013 | Waugh et al. | |
| 8,439,957 B2 | 5/2013 | Lombardo et al. | |
| 8,486,115 B2 | 7/2013 | Fisher et al. | |
| 2008/0249569 A1* | 10/2008 | Waugh ............... | A61F 2/30721 606/249 |
| 2013/0274747 A1 | 10/2013 | Fagan et al. | |
| 2014/0222086 A1 | 8/2014 | Kuster | |

* cited by examiner

*Primary Examiner* — Andrew Yang
(74) *Attorney, Agent, or Firm* — David L. King

(57) ABSTRACT

An improved spinal fusion system (10) for positioning between a first and second vertebral body, the system (10) has a body (100), a pair of polyaxial fasteners (220) and a locking bridge (102). The distal end has a slotted opening (120) extending through the body (100) and forming a gap extending between the two or more bore holes (110) to form a deflectable bridge (102) spanning the bore holes (110). The bridge (102) has a center opening (50) for receiving a set screw (20) passing through the bridge (102) into a threaded opening (52) in the body. When the set screw (20) is tightened, it deflects the bridge (102) closing the gap as the bridge (102) contacts an exterior surface of each head (210) of the polyaxial fasteners (200). The angulation of each polyaxial screw (200) is adjustable, controlled by the tightening of the set screw. Initial contact of the bridge (102) with the head (210) of the fastener (200) reduces angulation movement of the shank (220) requiring manual manipulation. Increased tightening of the set screw (20) fixes the angulation as the bridge (102) reduces the gap and increases fastener head contact forces.

7 Claims, 7 Drawing Sheets

SPINAL FUSION SYSTEM

TECHNICAL FIELD

Presented herein is a spinal fusion system. More specifically, a spinal fusion system for interbody implantation or corpectomy implantation in spine surgery.

BACKGROUND OF THE INVENTION

There are several procedures available to patients with degenerative spine conditions. For example, Anterior Lumbar Interbody Fusion ("ALIF") has been performed by surgeons since the 1950's. In an ALIF procedure, the disc space is fused by approaching the spine through the abdomen. In the ALIF approach, a three-inch to five-inch incision is made on the left side of the abdomen and the abdominal muscles are retracted to the side. Since the anterior abdominal muscle in the midline (rectus abdominis) runs vertically, it does not need to be cut and easily refracts to the side. The abdominal contents lay inside a large sack (peritoneum) that can also be refracted, thus allowing the spine surgeon access to the front of the spine without actually entering the abdomen. There is also a less popular transperitoneal approach that accesses the spine through the abdomen. This adds a lot of unnecessary morbidity to the procedure and therefore is used much less often.

Another technique is called Posterior Lumbar Interbody Fusion ("PLIF"). In the PLIF approach, the spine is accessed through a three-inch to six-inch long incision in the midline of the back and the left and right lower back muscles are stripped off the lamina on both sides and at multiple levels. After the spine is approached, the lamina is removed, which allows visualization of the nerve roots. The facet joints, which are directly over the nerve roots, may then be undercut to give the nerve roots more room. The nerve roots are then retracted to one side and the disc space is cleaned of the disc material. A bone graft, or an interbody cage, is then inserted into the disc space and the bone grows from vertebral body to vertebral body.

Still another procedure is a Transforaminal Lumbar Interbody Fusion ("TLIF"). By removing the entire facet joint, visualization into the disc space is improved and more disc material can be removed. It should also provide for less nerve retraction. Because one entire facet is removed, it is only done on one side. Removing the facet joints on both sides of the spine would result in too much instability. With increased visualization and room for dissection, a larger implant and/or bone graft can be used. Although this has some improvements over a PLIF procedure, the anterior approach, in most cases still provides the best visualization, most surface area for healing, and the best reduction of any of the approaches to the disc space.

There are other approaches know in the art, as well. For instance, Direct Lateral Interbody Fusion, Axial Lift using a transsacral approach, and the like. Additionally, there are similarly pluralities of methods for correcting degenerative issues with the cervical spine. Those skilled in the art will appreciate that these and other known procedures have benefits, as well as disadvantages. As such, more beneficial approaches in the art are needed.

SUMMARY OF THE INVENTION

Presented herein are systems, methods, and apparatuses for spinal fusion. In one aspect, presented herein is a spinal fusion system for positioning between two vertebral bodies. As such, the system can be used as an interbody system, or as a disc replacement system. In one aspect, the system comprises a body that defines two fastener bores therethrough, where each bore is configured for receipt of at least one polyaxial fastener. In this aspect, each polyaxial fastener is configured for insertion into one of the two vertebral bodies.

An improved spinal fusion system for positioning between a first and second vertebral body, the system has a body, a pair of polyaxial fasteners and a locking bridge.

The body has a longitudinal axis and a posterior face. The body defining two fastener bores therethrough. Each bore configured for receipt of at least one polyaxial fastener. Each fastener having a threaded shank and an enlarged head, wherein each fastener is configured for insertion into adjacent vertebrae. The body has a proximal end portion and a distal end portion. The two or more bore holes passing through the distal portion are inclined so each fastener shank extends either above or below the proximal end portion. Each bore hole is configured to loosely hold the polyaxial fastener at the head. The distal end has a slotted opening extending through the body and forming a gap extending between the two or more bore holes to form a deflectable bridge spanning the bore holes. The bridge has a center opening for receiving a set screw passing through the bridge into a threaded opening in the body. The portion of the opening into the body is threaded to engage the set screw. When the set screw is tightened, it deflects the bridge closing the gap as the bridge contacts an exterior surface of each head of the polyaxial fasteners. The angulation of each polyaxial screw is adjustable, controlled by the tightening of the set screw. Initial contact of the bridge with the head of the fastener reduces angulation movement of the shank requiring manual manipulation. Increased tightening of the set screw fixes the angulation as the bridge reduces the gap and increases fastener head contact forces.

A preferred embodiment has a washer and wherein the set screw has a groove for receiving the washer. The washer holds the set screw at the groove. The washer is positioned in the slotted opening under the bridge aligned with the center opening.

Another feature of the preferred embodiment is a pair of inserter mounting connectors formed in the bridge. One connector is on each diametrically opposed side of the center opening. Each inserter mounting connector is a void region cut into an edge of the bridge. One is located at a top or first edge and an opposite one at a bottom or second edge to provide a clamping and gripping surface and orientation control during insertion into two adjacent vertebral bodies. Each connector is interior of a projected exterior profile of the body, this insures tissue does not tear or impact the insertion tool on implant insertion. Each void region is sized to accommodate an insertion tool within or inferior to the projected exterior profile of the distal end of the body.

Yet another feature provides an anti-screw back out device. Each bore hole has two projecting nubs extending from the bore hole interior surface on a side position within an angle of 120 degrees or less relative to the other, the nubs providing an anti-back out feature to retain the polyaxial fasteners in the body.

Related methods of operation are also provided. Other apparatuses, methods, systems, features, and advantages of the location module will be or become apparent to one with skill in the art upon examination of the following figures and detailed description. It is intended that all such additional apparatuses, methods, systems, features, and advantages be included within this description, be within the scope of the spinal fusion system, and be protected by the accompanying claims.

BRIEF DESCRIPTION OF THE DRAWINGS

The invention will be described by way of example and with reference to the accompanying drawings in which.

DETAILED DESCRIPTION OF THE INVENTION

Figure 1:
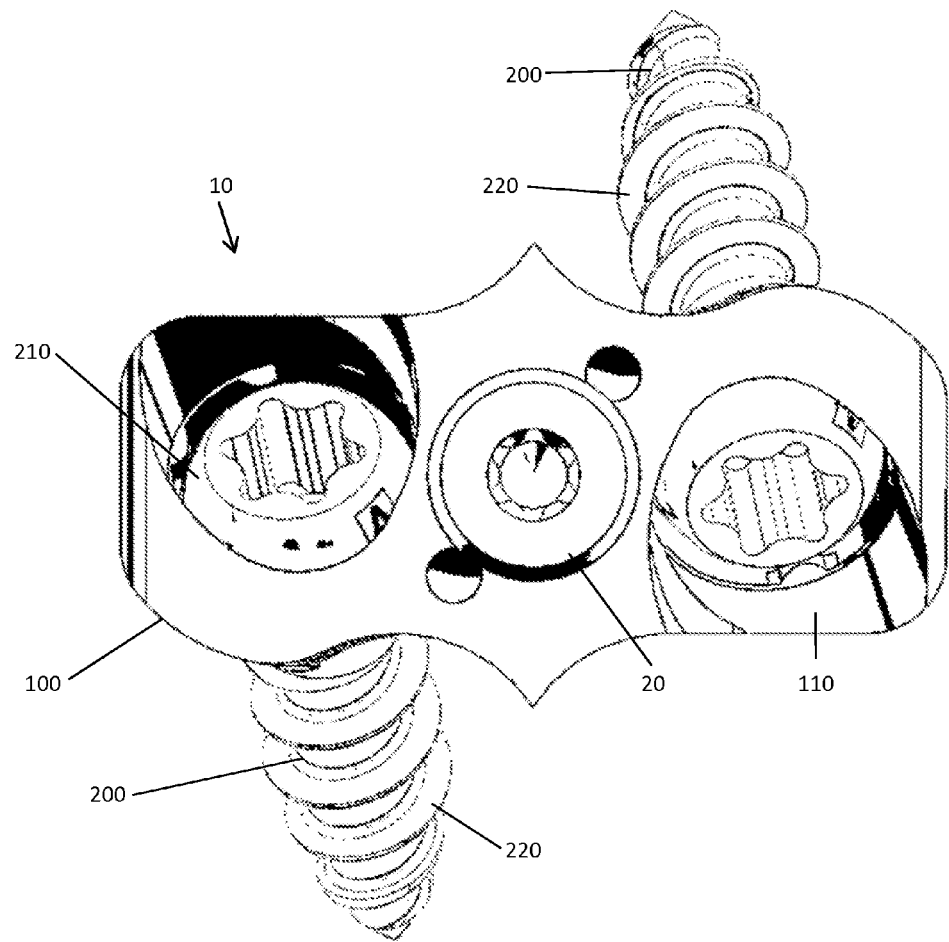
FIG. 1 is a distal end view of a first embodiment spinal fusion system.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein are systems, methods, and apparatuses for spinal fusion. In one aspect, presented herein is a spinal fusion system 10 for positioning between two vertebral bodies, which in most cases are adjacent one another. As such, the system can be used as an interbody system, or as a partial or full disc replacement system. In one aspect, the system comprises a body 100 having a longitudinal axis. The body 100 defines at least one fastener bore 110 therethrough, where each bore is configured for receipt of two fasteners 200. In this aspect, each fastener 200 is configured for insertion into one of the first or second vertebral bodies 15, 17.

Figure 7:
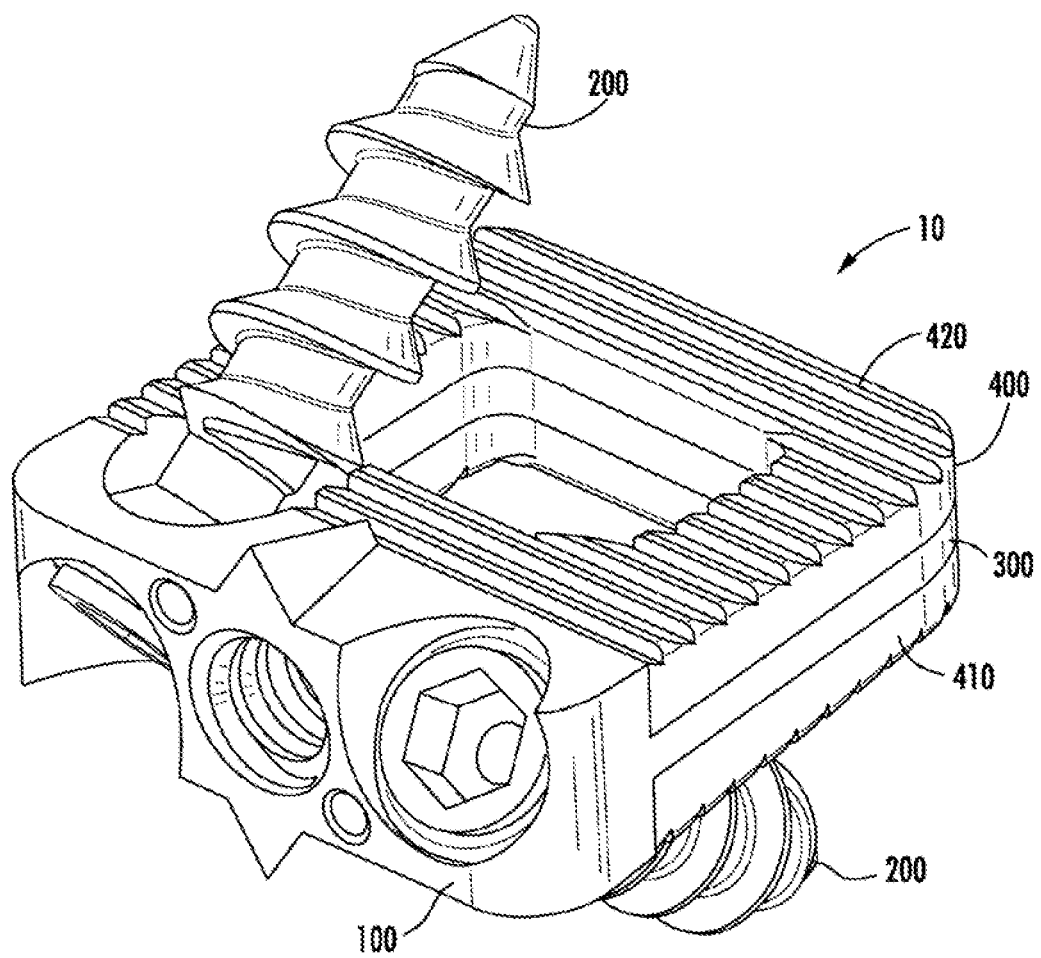
FIG. 7 is an embodiment disclosed in co-pending patent application U.S. Ser. No. 13/225,708 (US Publication 2013/0060336).

The spinal fusion system which was described in co-pending US Patent Publication US 2013/0060336 is hereby being incorporated by reference herein in its entirety. In that spinal fusion system, the system focused on the use of a substantially rigid body that had a first modulus of elasticity and two opposing portions or implant bodies 400, 410 as shown in FIG. 7 each having a lower modulus. In another aspect, the system comprises a substantially rigid plate 300 connected to a portion of the posterior face of the substantially rigid body 100 that extends away from and substantially transverse to the posterior face of the substantially rigid body. In one aspect, the system has a first implant body 400 and a second implant body 410, where each body has a modulus of elasticity less than or equal to the first modulus of elasticity of the substantially rigid plate 300. The first and second implant bodies are configured to matingly connect to one another with at least a portion of the substantially rigid plate positioned therebetween. As such, the combination of the first and second implant bodies and the substantially rigid plate is configured for insertion between the two vertebral bodies. In the case of a corpectomy, the combination can be inserted in the space made by the either partial or full removal of a disc.

The thickness of the first and second implant bodies can vary according to the need of the surgeon and the anatomy of the patient. The thickness of the two bodies can be equal or either one of them can be thicker than the other, depending upon the particular circumstance. Additionally, as one skilled in the art can appreciate, the first implant body 400 can comprise the same material as the second implant body 410. However, it may also differ in composition. In one aspect, the first implant body comprises a thermoplastic material. As such, in another aspect the second implant body can also comprise a thermoplastic material. In yet another aspect, the thermoplastic material can comprise polyetheretherketone.

In one aspect, the substantially rigid plate 300 is substantially bisected by a first plane P that contains the longitudinal axis. Yet, in other aspects, the substantially rigid plate 300 can be in a plane that is offset from the longitudinal axis.

The substantially rigid plate and the substantially rigid body 100 can be connected in various common means. However, in one aspect, the substantially rigid body and the substantially rigid plate are integral.

As mentioned above, the substantially rigid body defines at least one fastener bore 110 therethrough, where each bore is configured for receipt of at least one fastener such that a fastener 200 can be inserted into one of the first or second vertebral bodies. In one aspect, there can be a plurality of fastener bores with corresponding fasteners. In an exemplified aspect, at least one of the fasteners can be angled upwardly with respect to the first plane and another fastener can be angled downwardly with respect to the first plane.

Although, it is contemplated that the fasteners are disposed at various angles, in one aspect, the first and second fasteners are oppositely disposed at substantially equal angles .alpha. In another aspect, the substantially equal angles are between about 20 degrees and about 45 degrees. In still another aspect, the angles are about 35 degrees.

While various materials of construction suitable for implantation into the human body are contemplated, in one aspect, at least one of the substantially rigid plate and the substantially rigid body 100 comprises titanium. In other aspect, both the rigid plate and rigid body comprise titanium.

As shown, the first implant body 400 and the second implant body 410 each have a first and second surface and wherein the first implant body and the second implant body connect at their respective first surfaces. In one aspect, at least one of the second surfaces of the first implant body and the second implant body are ramped downwardly away from the substantially rigid body 100. In another aspect, both bodies have second surfaces that are ramped downwardly away from the substantially rigid body 100. This configuration makes insertion easier.

In yet another exemplified aspect, at least one of the second surfaces of the first implant body 400 and the second implant body 410 define ridges 420. It is also contemplated that both second surfaces define ridges 420 to assist in retaining the system between the two vertebral bodies.

All of the above features shown in FIG. 7 can be employed in the new improved spinal fusion system disclosed hereinafter.

Figure 2:
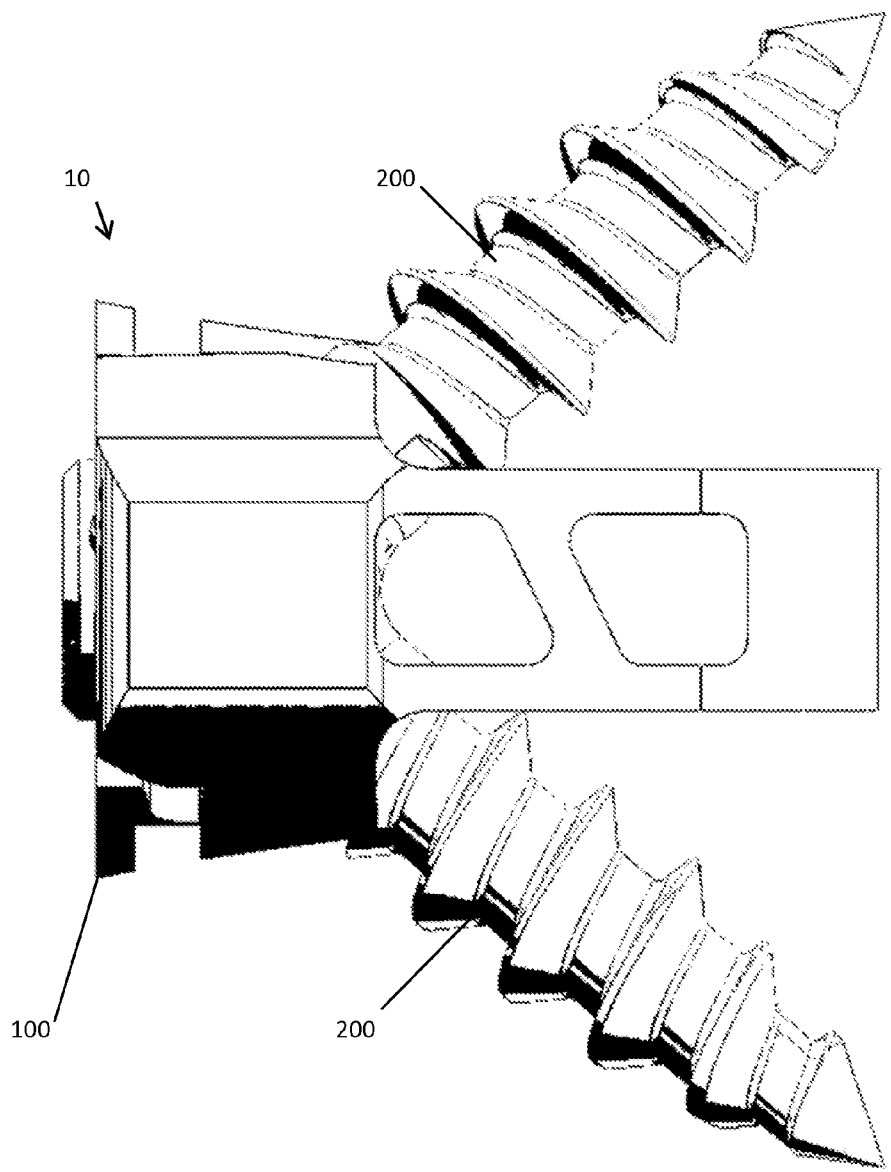
FIG. 2 is a side view of the spinal fusion system of FIG. 1.
Figure 3:
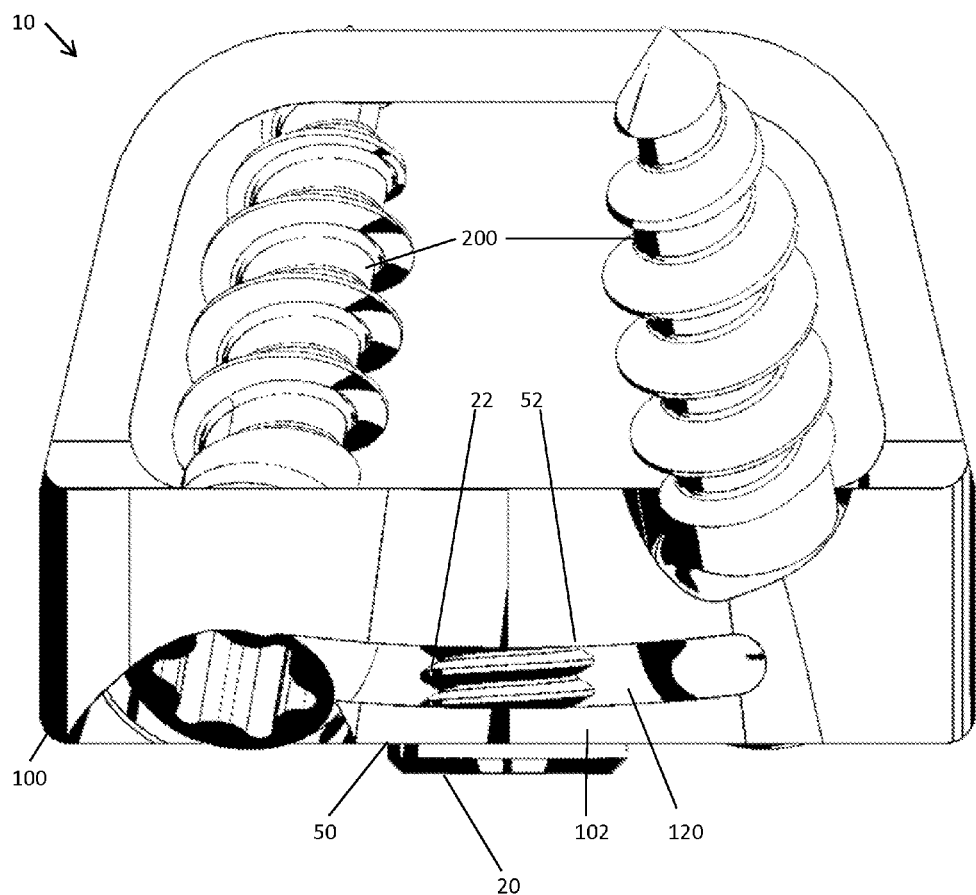
FIG. 3 is a top elevational view of the spinal fusion system of FIG. 1.

With reference to FIGS. 1-3, a first embodiment of the invention is illustrated. This spinal implant system 10, as shown in FIG. 1, has a body 100 with bore holes 110 extending from a distal end inwardly to receive polyaxial fasteners 200, the bore holes 110 provide a means through which the fasteners 200 can be held at the head 210 by the body 100 inside the bore hole 110. These fasteners 200 are polyaxial in that they can change angulation of the threaded shank 220 directionally to facilitate insertion into a vertebrae body. As further shown in FIG. 1, a set screw 20 is shown centered on opening 50 in the body 100. With reference to FIG. 2, a side view illustrates the angulation of the fasteners 200 relative to the body 100. With reference to FIG. 3, the set screw 20 is shown extending through the opening 50 in the body 100 wherein a slotted opening 120 has been created that extends through the body 100 open on both sides in such a fashion that the set screw 20 threads 22 can threadingly engage a threaded opening 52 in a lower portion of the body 100 below the slot 120. This slot 120 creates a bridge 102 that spans between the two bore holes 110. The bridge 102 as illustrated, is gapped a sufficient amount or distance above the lower portion of the body 100 spaced by the slot 120 directly below the bridge 102. As the set screw 20 is tightened, the edges of the bridge 102 adjacent the bore holes 110 can come into contact with an exterior surface of the screw head 210 of the polyaxial fasteners 200. This ability to tighten the set screw 20 thereby tightening and deflecting the bridge 102 so that the gap is reduced allows the angulation of the threaded fasteners 200 to be fixed when the set screw 20 is slightly tightened such that the head 210 is contacted with a minimal amount of force making it possible to still move the threaded shank portion 220 to change angulation. As the set screw 20 is tightened further the ability to move or manipulate the threaded shank 220 is reduced greatly to the point where the fasteners 200 are effectively fixed in their angulation.

Figure 4:
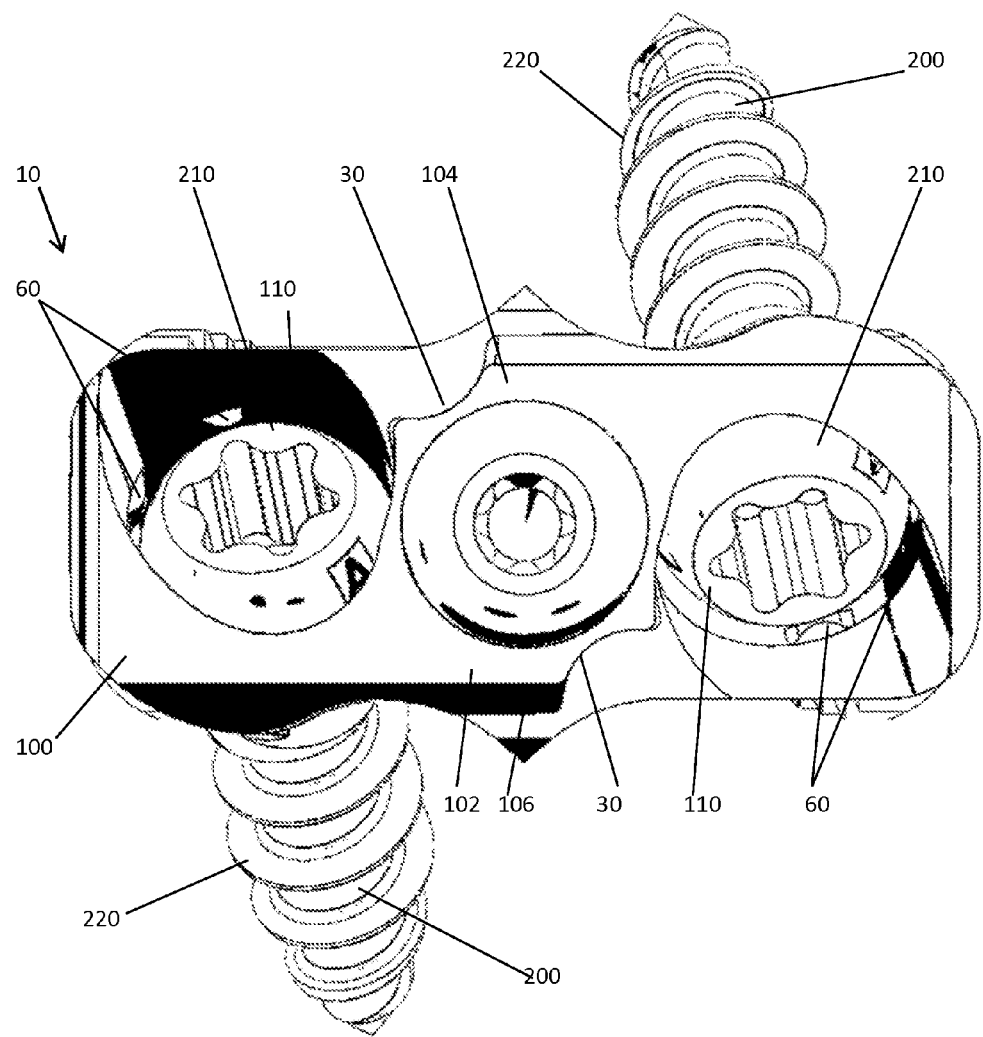
FIG. 4 is a distal end view of a second embodiment of the spinal fusion system.
Figure 5:
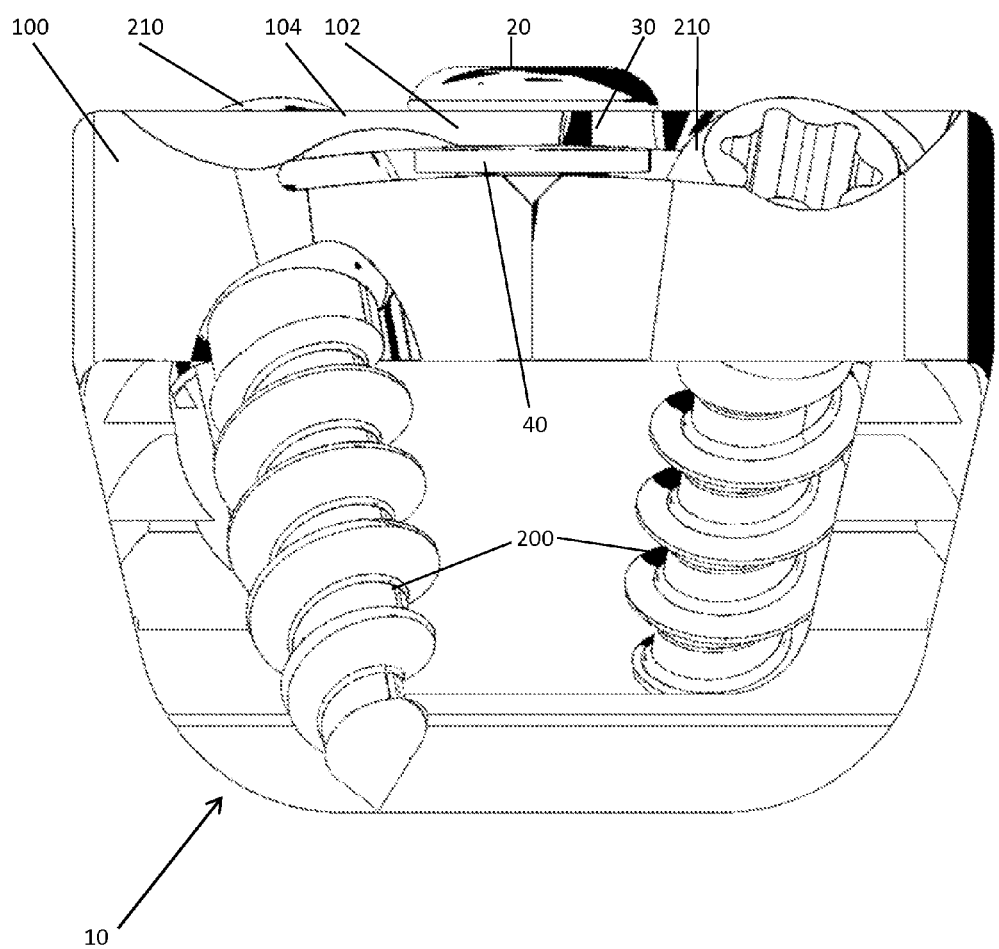
FIG. 5 is a top plan view of the second embodiment of the spinal fusion system of FIG. 4.
Figure 6:
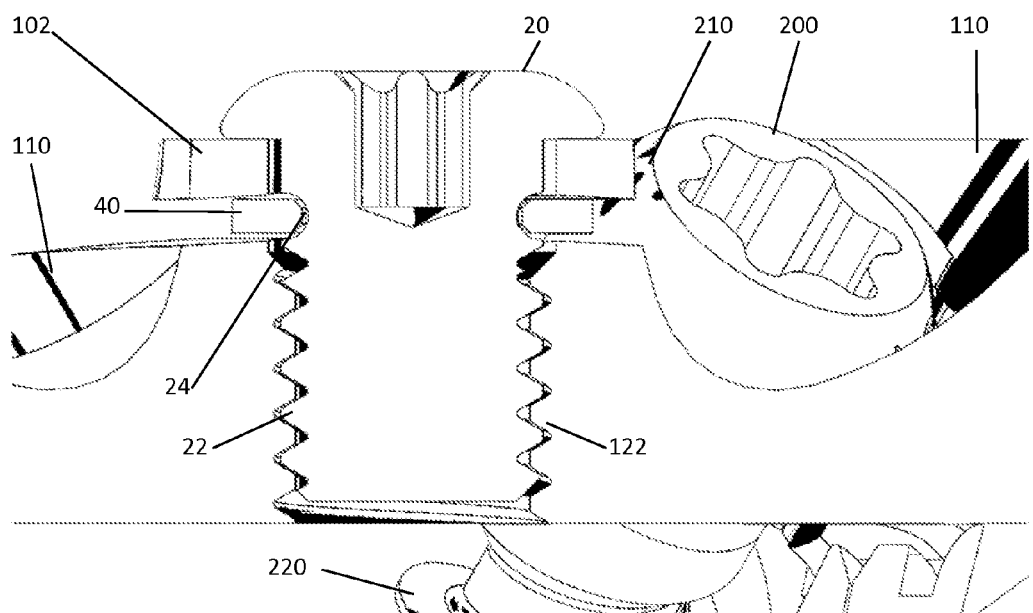
FIG. 6 is an enlarged cross sectional view of the body of the second embodiment spinal fusion system.

With reference to a second embodiment illustrated in FIGS. 4-6, the second embodiment has all the features of the first embodiment; however, provides additional features such as the bridge 102 includes inserter mounting connectors 30. The inserter mounting connectors 30 are cutouts or voids in the bridge 102, the bridge having a bottom or second edge 106 and a top or first edge 104 from which the cutout portions or regions that form the connector 30 are shown. The connector 30 extends into the bore opening 110 and creates a large void on each diametrically opposed side of the set screw 20. As shown, these inserter mounting connectors 30 are diametrically opposed on opposite sides of the set screw 20 angled such that they create a pair of excellent clamping and gripping access points for an insertion tool (not shown). The connectors 30 as illustrated are well within inside the exterior projected profile of the body 100 as can be illustrated in FIG. 4. This means that any insertion tool can be placed interior of the exterior projected profile surfaces of the implant. This means that on insertion between vertebral bodies any tissue that drags along the body will not impact directly on a leading surface of an insertion tool because the body 100 profile exceeds that location. This will minimize any tissue damage during the insertion of the device. As further shown in FIG. 4, two projecting nubs 60 are shown extending outwardly from an interior surface of the bores 110. These nubs 60 project inwardly in such a fashion that they form an included of less than 120 degrees and directionally are all on one side of a head 210 of a fastener 200. When the fastener 200 is placed in the bore hole 110 it must move past these projections 60. Once past the projections 60, the fastener 200 cannot fall out of the implant or back out. This retains the threaded fasteners 200 in position as an assembly to the improved spinal fusion implant device. As such, these fasteners 200 are held in place and will not fall out of the device.

With reference to FIG. 5, another improved feature of the present invention is that the set screw 20 is surmounted by a washer 40. This washer 40 is positioned in the gap or slotted opening 120 formed under the bridge 102 and as such provides a means for holding the set screw 20 in place that will prevent it from ever loosening or coming apart. With reference to FIG. 6, the washer 40 is shown positioned in a groove 24 cut into the set screw 20, the washer 40 snaps into place onto this groove 24 as the set screw 20 is positioned into the device body 100 at opening 50. As can be seen, the washer 40 has a thickness sufficiently narrower than the gap created. This allows the set screw 20 to be able to pull directly onto the threads 122 within the body 100 as it is tightened closing the gap under the bridge 102 in such a fashion that the bridge 102 comes into contact with the head 210 of the fastener 200 locking it into position as previously discussed. The advantage of this improved set screw 20 washer 40 combination is that the surgeon will not have to worry about the set screw 20 ever loosening or coming apart. Once the fasteners 200 are threaded into the vertebrae, the washer 40 and set screw 20 will have achieved their purpose of locking the components in position. As shown, the body 100 is preferably made from titanium, or other materials can be used and as previously mentioned, the body may include a rigid portion that is made of a titanium or other implantable material and may also include a more elastic exterior ridged surface as previously discussed in the co-pending application. It is important however to understand that the present improved version of this spinal fusion system provides means for locking the fasteners 200 into position that is usable with virtually any spinal implant wherein the fasteners 200 are positioned as indicated.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An improved spinal fusion system for positioning between a first and second vertebral body, the system comprising:

a body having a longitudinal axis and a posterior face, the body defining two fastener bores therethrough, each bore configured for receipt of at least one polyaxial fastener, each fastener having a threaded shank and an enlarged head, wherein each fastener is configured for insertion into adjacent vertebrae, the body having a proximal end portion and a distal end portion, the two or more bore holes passing through the distal portion being inclined so each fastener shank extends either above or below the proximal end portion, each bore hole configured to loosely hold the polyaxial fastener at the head, the distal end having a slotted opening extending through the body and forming a gap extending between the two or more bore holes to form a deflectable bridge spanning the bore holes, the bridge has a center opening for receiving a set screw passing through the bridge into a threaded opening in the body, a portion of the opening into the body being threaded to engage the set screw, and wherein the set screw when tightened deflects the bridge closing the gap as the bridge contacts an exterior surface of each head of the polyaxial fasteners.

2. The improved spinal fusion system of claim 1 wherein the angulation of each polyaxial screw is adjustable, controlled by the tightening of the set screw, initial contact of the bridge with the head of the fastener reduces angulation movement of the shank requiring manual manipulation, increased tightening of the set screw fixes the angulation as the bridge reduces the gap and increases fastener head contact forces.

3. The improved spinal fusion system of claim 1 further comprises a washer, wherein the set screw has a groove for receiving the washer, the washer holds the set at the groove, the washer being positioned in the slotted opening under the bridge aligned with the center opening.

4. The improved spinal fusion system of claim 1 further comprises a pair of inserter mounting connectors formed in the bridge, one connector being on each diametrically opposed side of the center opening.

5. The improved spinal fusion system of claim 4 wherein each inserter mounting connector is a void region cut into an edge of the bridge, one being located at a top or first edge and an opposite one at a bottom or second edge to provide a clamping and gripping surface and orientation control during insertion into two adjacent vertebral bodies, each connector being interior of a projected exterior profile of the body.

6. The improved spinal fusion system of claim 5 wherein each void region is sized to accommodate an insertion tool within or inferior to the projected exterior profile of the distal end of the body.

7. The improved spinal fusion system of claim 1 wherein each bore hole has two projecting nubs extending from the bore hole interior surface on a side position within an angle of 120 degrees or less relative to the other, the nubs providing an anti-back out feature to retain the polyaxial fasteners in the body.

* * * * *